United States Patent [19]

Sugimoto et al.

[11] Patent Number: 5,187,749

[45] Date of Patent: Feb. 16, 1993

[54] VIRUS INFECTION EXAMINATION APPARATUS HAVING AUTOMATIC DETERMINATION FUNCTION AND METHOD THEREFOR

[75] Inventors: Yukihiro Sugimoto, Tokyo; Toru Kakubari, Hachioji, both of Japan

[73] Assignee: Olympus Optical Co., Ltd., Tokyo, Japan

[21] Appl. No.: 679,906

[22] Filed: Apr. 3, 1991

[30] Foreign Application Priority Data

Apr. 10, 1990 [JP] Japan ................................. 2-94732

[51] Int. Cl.$^5$ ........................ G06K 9/00; G06F 15/00
[52] U.S. Cl. .......................................... 382/6; 356/39; 364/413.08; 435/5
[58] Field of Search .................... 382/6; 356/39; 364/413.08, 413.07, 413.1; 435/5

[56] References Cited

U.S. PATENT DOCUMENTS

| | | | |
|---|---|---|---|
| 3,916,205 | 10/1975 | Kleinerman | 356/39 |
| 4,125,828 | 11/1978 | Resnick et al. | 382/6 |
| 4,191,940 | 3/1980 | Polcyn et al. | 356/39 |
| 4,983,359 | 1/1991 | Tomioka et al. | 356/39 |
| 5,086,476 | 2/1992 | Bacus | 382/6 |

FOREIGN PATENT DOCUMENTS 61-247962 11/1986 Japan .
63-140960 6/1988 Japan .
63-231263 9/1988 Japan .

OTHER PUBLICATIONS

Toxicology Forum Vo. 11 (6), 642–652, 1988 "Titration of Human Immuno-Deficiency Virus (HIV)".

Primary Examiner—Leo H. Boudreau
Attorney, Agent, or Firm—Frishauf, Holtz, Goodman & Woodward

[57] ABSTRACT

A virus infection examination apparatus includes a microscope for observing fluorescent images of antigen positive and negative cells dyed with a fluor by an indirect fluorescent antibody method using a serum of an object to be examined. An image pickup unit converts the fluorescent images as observation images of the microscope into image data. A detection unit processes the image data obtained by the image pickup unit and detects intracellular luminance distributions. A determination unit determines the presence/absence of a virus infection of the object on the basis of a difference between the fluorescent luminance distributions detected by the detecting unit.

5 Claims, 12 Drawing Sheets

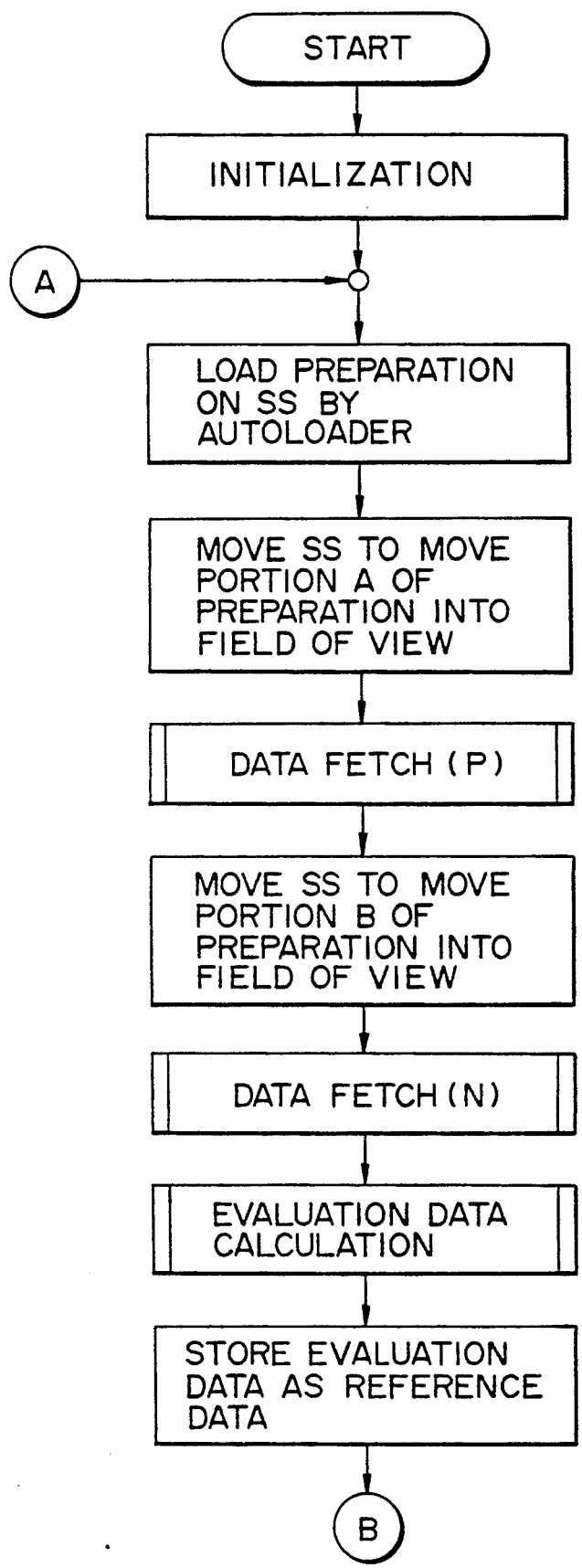
F I G. 2A

DYE a

DYE b (WHEN OBJECT TO BE EXAMINED IS INFECTED WITH VIRUS)

(WHEN OBJECT TO BE EXAMINED IS NOT INFECTED WITH VIRUS)

(WHEN NONSPECIFIC REACTION IS CAUSED)

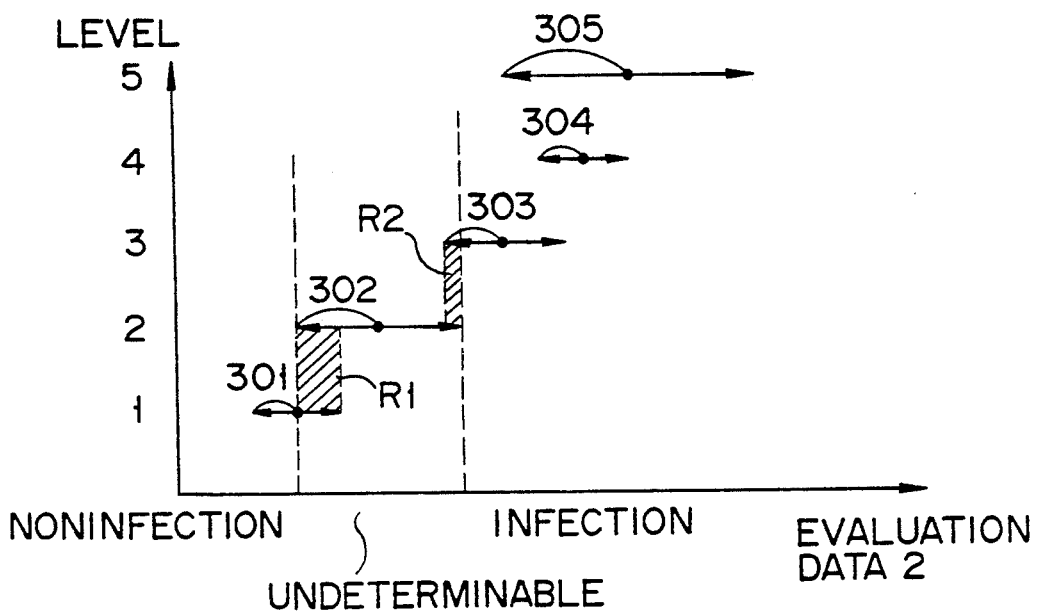
F I G. 12A
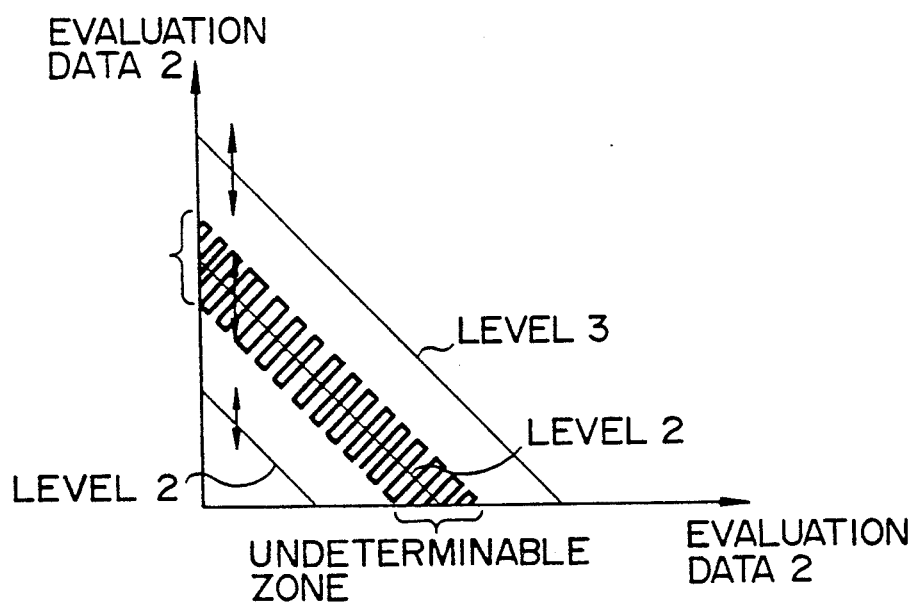
F I G. 12B

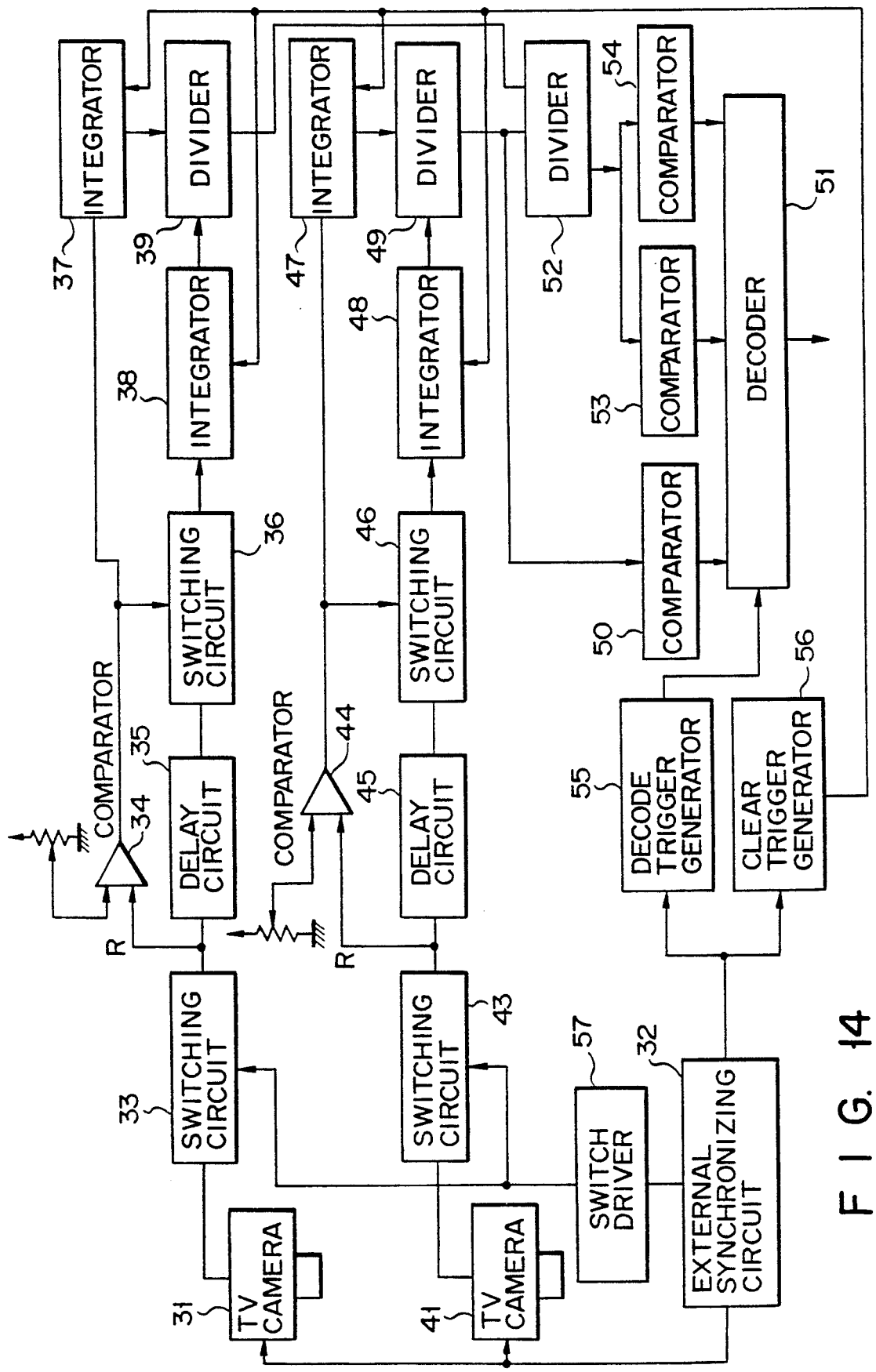
F I G. 14

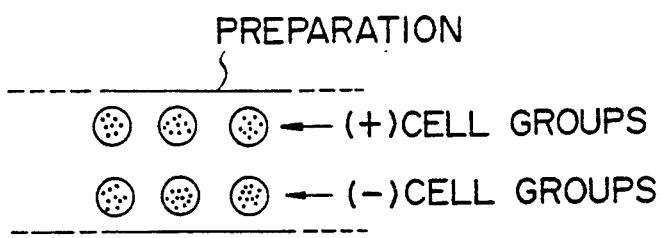
FIG. 15
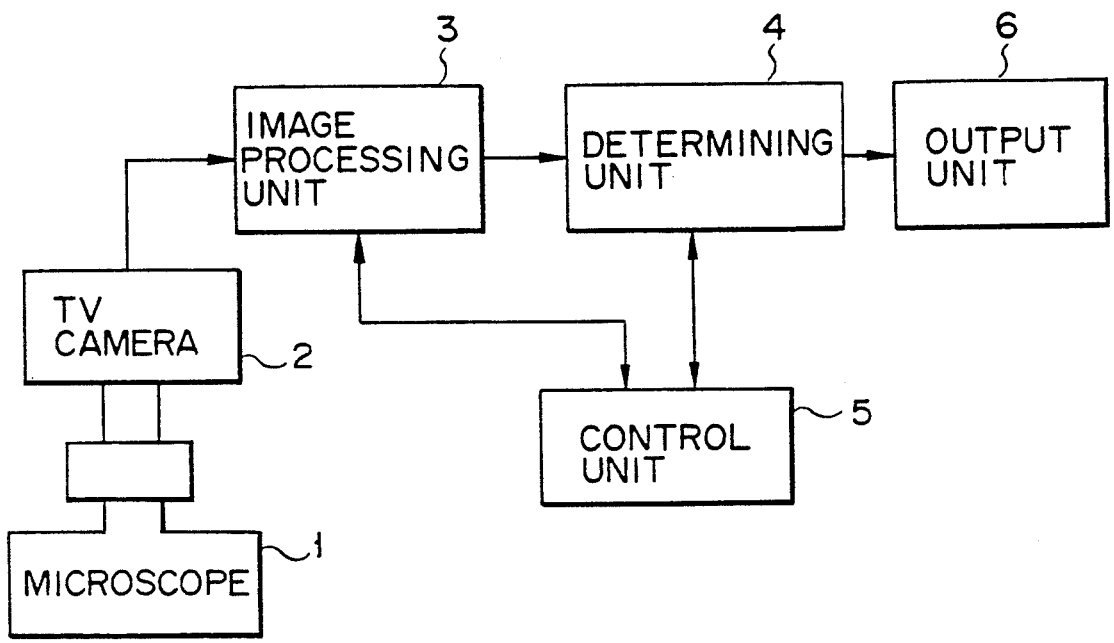
FIG. 16
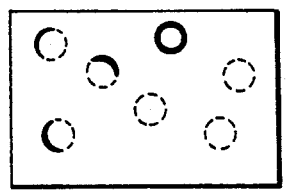 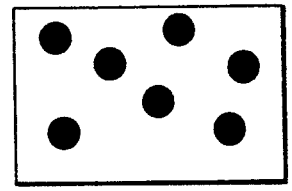
FIG. 17A    FIG. 17B

VIRUS INFECTION EXAMINATION APPARATUS HAVING AUTOMATIC DETERMINATION FUNCTION AND METHOD THEREFOR

BACKGROUND OF THE INVENTION

1. Field of the Invention

The present invention relates to a virus infection examination apparatus and a virus infection examination method, which automatically examine the presence/absence of virus infections of an object to be examined using an indirect fluorescent antibody method.

2. Description of the Related Art

An indirect fluorescent antibody method has been conventionally known as a method of examining the presence/absence of virus infections. In this method, a fluorescent image of a sample is observed to check whether an object to be examined has an antibody against (i.e., is infected with) a specific virus. The indirect fluorescent antibody method is executed at the level of reexamination of people who are determined to be positive in a screening examination of, e.g., an ATL virus (adult T-cell leukemia) or an HIV virus (AIDS). The virus infection examination according to the indirect fluorescent antibody method is performed by the following procedures.

(1) Leukocytes of a virus-infected body which is infected with a virus to be examined are fixed on a preparation.

(2) A serum of an object to be examined is reacted with the leukocytes of the virus-infected body and then washed away. In this case, if the object is infected with the virus, he or she has an antibody A against the virus. Therefore, his or her serum is not washed away but remains since it is bonded to the leukocytes.

(3) Subsequently, an antibody B which can be bonded to the antibody A of the object and is marked with a fluor is reacted with the leukocytes and then washed away. In this case, if the antibody A remains in procedure (2) above, the antibody B is not washed away but remains since it is bonded to the antibody A.

When an examiner observes the sample formed by procedures (1) to (3) above by using a microscope, a fluorescent image can be observed if the object to be examined is infected with the virus. Therefore, whether the object is infected can be determined from this fluorescent image.

Since, however, this conventional virus infection examination using the indirect fluorescent antibody method depends on determination based on the experimental knowledge of a skilled examiner, the burden on the examiner is increased to make it impossible to examine a large number of objects. Also, it is difficult to maintain high reliability.

In addition, if an object to be examined suffers from an autoimmune disease, since the reaction with cells occurs in a nonspecific manner, it is difficult to distinguish the disease from virus infections.

Furthermore, if the antibody valence of an antibody is small, an antigen-antibody reaction occurs less easily. Therefore, the fluorescent intensity of a fluorescent image is weakened to make it difficult to distinguish this infection from a noninfected state. In addition, light is emitted when washing is imperfect or a sample is contaminated to easily lead to erroneous determination.

SUMMARY OF THE INVENTION

It is, therefore, the first object of the present invention to provide a virus infection examination apparatus which can largely reduce the burden on an examiner and can obtain a highly reliable determination result.

It is the second object of the present invention to provide a virus infection examination method which can largely reduce the burden on an examiner and can obtain a highly reliable determination result.

In order to achieve the first object according to an aspect of the present invention, there is provided a virus infection examination apparatus comprising:

a microscope for observing fluorescent images of antigen positive and negative cells dyed with a fluor by an indirect fluorescent antibody method using a serum of an object to be examined;

image pickup means for converting the fluorescent images as observation images of the microscope into image data;

detecting means for processing the image data obtained by the image pickup means and detecting fluorescent luminance distributions of the antigen positive and negative cells; and means for determining the presence/absence of a virus infection of the object on the basis of a difference between the fluorescent luminance distributions detected by the detecting means.

In order to achieve the second object according to another aspect of the present invention, there is provided a virus infection examination method for examining a virus infection of an object to be examined from fluorescent images of cells dyed with a fluor by an indirect fluorescent antibody method using a serum of the object, comprising the steps of:

a first dyeing step of dyeing antigen positive and negative cells with a predetermined dye color in accordance with the indirect fluorescent antibody method;

a second dyeing step of dyeing all the cells in a dye color different from the predetermined dye color in the first dyeing step;

checking cell positions on the basis of a fluorescent image obtained in the second dyeing step; and determining the virus infection of the object on the basis of the fluorescent image obtained in the first dyeing step.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIGS. 2A and 2B are flow charts showing an operation of the first embodiment;

FIG. 12A is a graph showing threshold values for determination obtained when the evaluation data is "1";

FIG. 12B is a graph showing threshold values obtained when the evaluation data is "2";

FIG. 14 is a block diagram showing the second embodiment of the present invention;

FIG. 15 is a plan view showing a preparation;

FIG. 16 is a block diagram for explaining the principle of a virus infection examination apparatus; and FIGS. 17A and 17B are views showing fluorescent images.

DETAILED DESCRIPTION OF THE PREFERRED EMBODIMENTS

Figure 1:
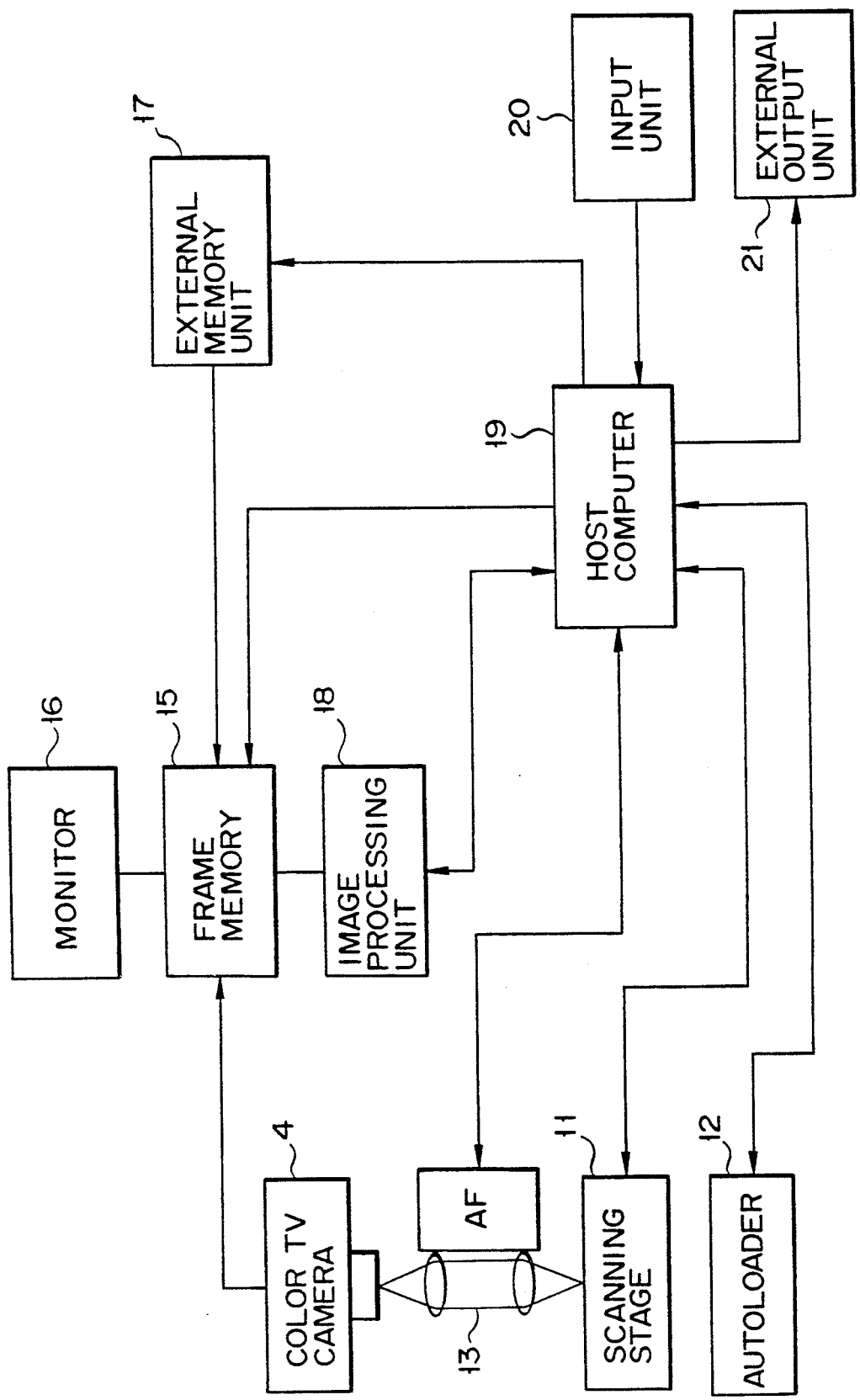
FIG. 1 is a block diagram showing the first embodiment of the present invention.
Figure 2B:
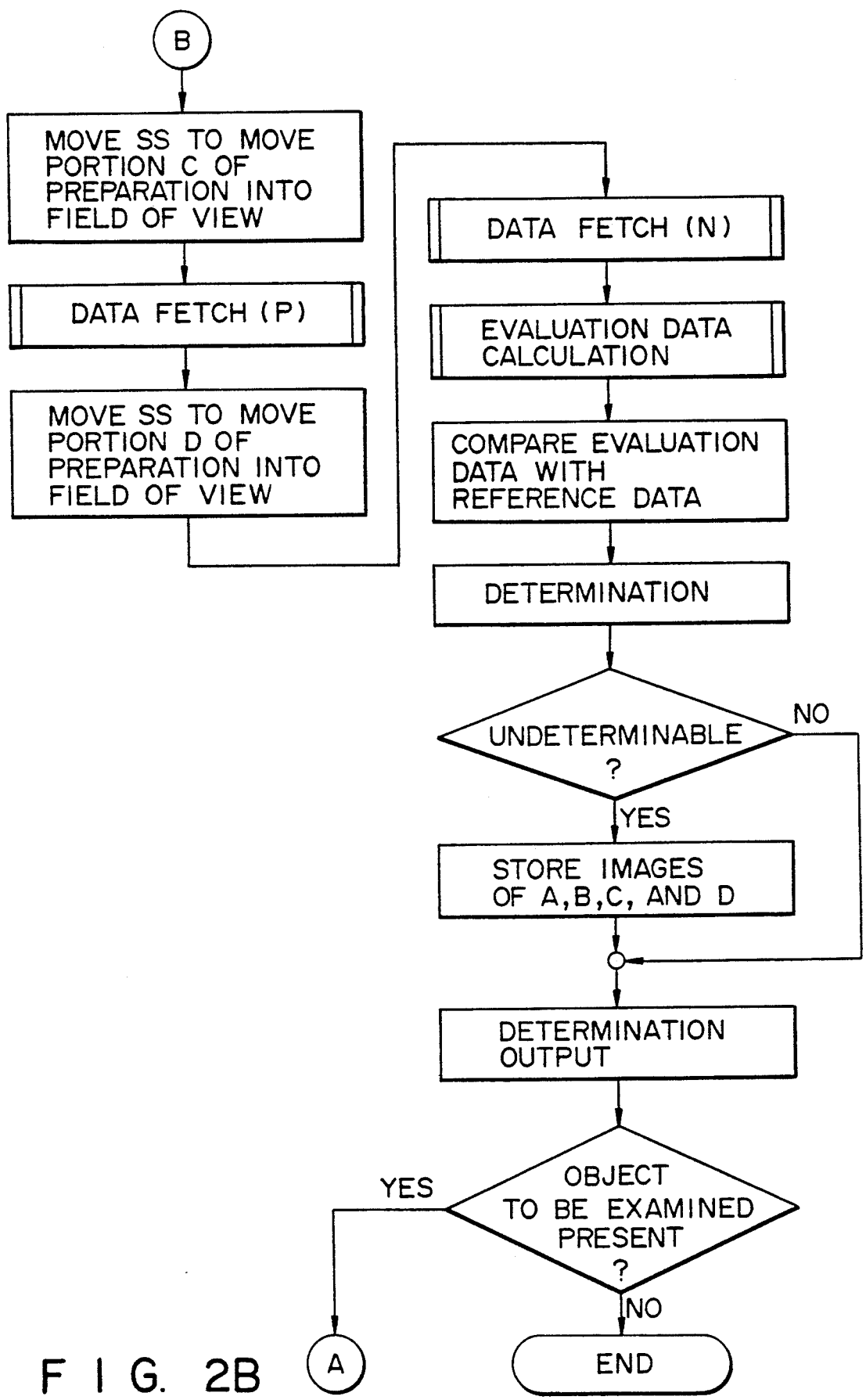

Before description of preferred embodiments of the present invention, a virus infection examination principle according to the present invention will be described below with reference to FIGS. 15 and 16.

First, antigen positive cell ((+)cell) groups and antigen negative cell ((−)cell) groups are independently arranged on a preparation shown in FIG. 15 and dyed by an indirect fluorescent antibody method to form samples.

Subsequently, the formed samples are examined by an examination system shown in FIG. 16. That is, each formed sample is observed by a microscope 1, and an observed image is converted into image data by a TV camera 2 and fetched in an image processing unit 3. Examples of the observed image to be fetched in the image processing unit 3 are a fluorescent image (17A) in which only some of cells emit light and a fluorescent image (17B) in which all cells emit light. The image processing unit 3 analyzes such a fluorescent image to detect fluorescent luminance distributions inside and outside cells and supplies the detection data to a determining unit 4. The determining unit 4 calculates a characteristic value of the extracellular fluorescent luminance distribution and determines that the condition of the sample is bad if the characteristic value of the extracellular fluorescent luminance distribution exceeds a predetermined threshold value. In addition, the determining unit 4 detects a (−)cell in a good condition and calculates a characteristic value of an intra(−)cellular fluorescent luminance distribution of the (−)cell. If the characteristic value exceeds a predetermined threshold value, the determining unit 4 determines that the sample is causing a nonspecific reaction. The determining unit 4 obtains the intra(−)cellular and intra(+)cellular fluorescent luminance distributions and compares the two luminance distributions to calculate a characteristic value of an object to be examined, thereby determining infection, noninfection, and an undeterminable state in accordance with a predetermined determination reference. The operations of the image processing unit 3 and the determining unit 4 are controlled by a control unit 5, and the determination result of the determining unit 4 is output to an output unit 6.

Embodiments of the present invention will be described below.

FIG. 1 is a block diagram showing a virus infection examination apparatus according to the first embodiment of the present invention. Referring to FIG. 1, reference numeral 11 denotes a scanning stage (SS) movable in the X and Y directions, and preparations on which samples are arranged are automatically, sequentially loaded on the SS 11 by an autoloader 12. The samples on the preparation loaded on the SS 11 are observed by a microscope 13 using an auto-focusing function. A color TV camera 14 is provided such that an observed image of the microscope 13 is focused on its light-receiving surface. The camera 14 picks up the observed image, converts the image into electrical image data, and outputs the image data to a frame memory 15. The image data in the frame memory 15 is visualized and displayed on a monitor 16. In addition, transmission/reception of the image data is executed with respect to the external memory unit 17. The image data in the frame memory 15 is supplied to an image processing unit 18. The image processing unit 18 has an analyzing function (to be described later) and outputs the analysis result to a host computer 19. The host computer 19 receives, from an input unit 20, evaluation data, designation of a threshold value, and a command for reading out the stored image data. In addition, the host computer 19 checks the presence/absence of a virus infection of an object in accordance with the evaluation data and the analysis result and outputs the determination result to an external output unit 21.

The host computer 19 operates on the basis of flow charts shown in FIGS. 2A to 4 and has functions of, e.g., controlling an image data fetch operation, forming evaluation data, and determining virus infections.

Figure 5:
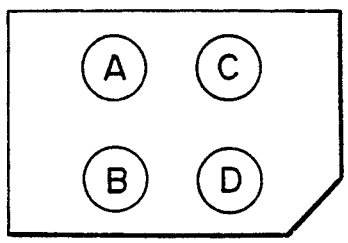
FIG. 5 is a plan view showing a preparation.

Each preparation to be loaded on the SS 11 by the autoloader 12 has a rectangular shape as a whole and is cut at its one corner, as shown in FIG. 5, so as to be set in only one predetermined direction on the autoloader 12.

Figure 6:
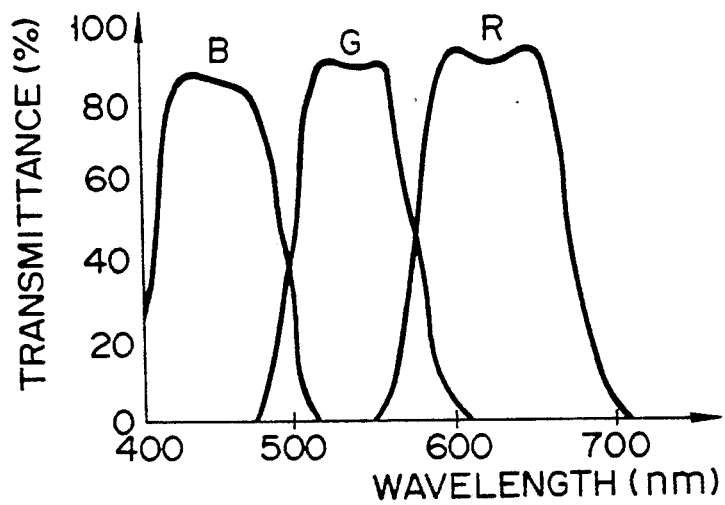
FIG. 6 is a graph showing spectral sensitivity characteristics of a TV camera.

Frames of red, green, and blue of the color TV camera 14 have spectral sensitivity characteristics as shown in FIG. 6, and sample images of a preparation fetched in accordance with these spectral sensitivity characteristics are stored in the frame memory 15.

An operation of this embodiment will be described below with reference to FIG. 3.

Figure 3:
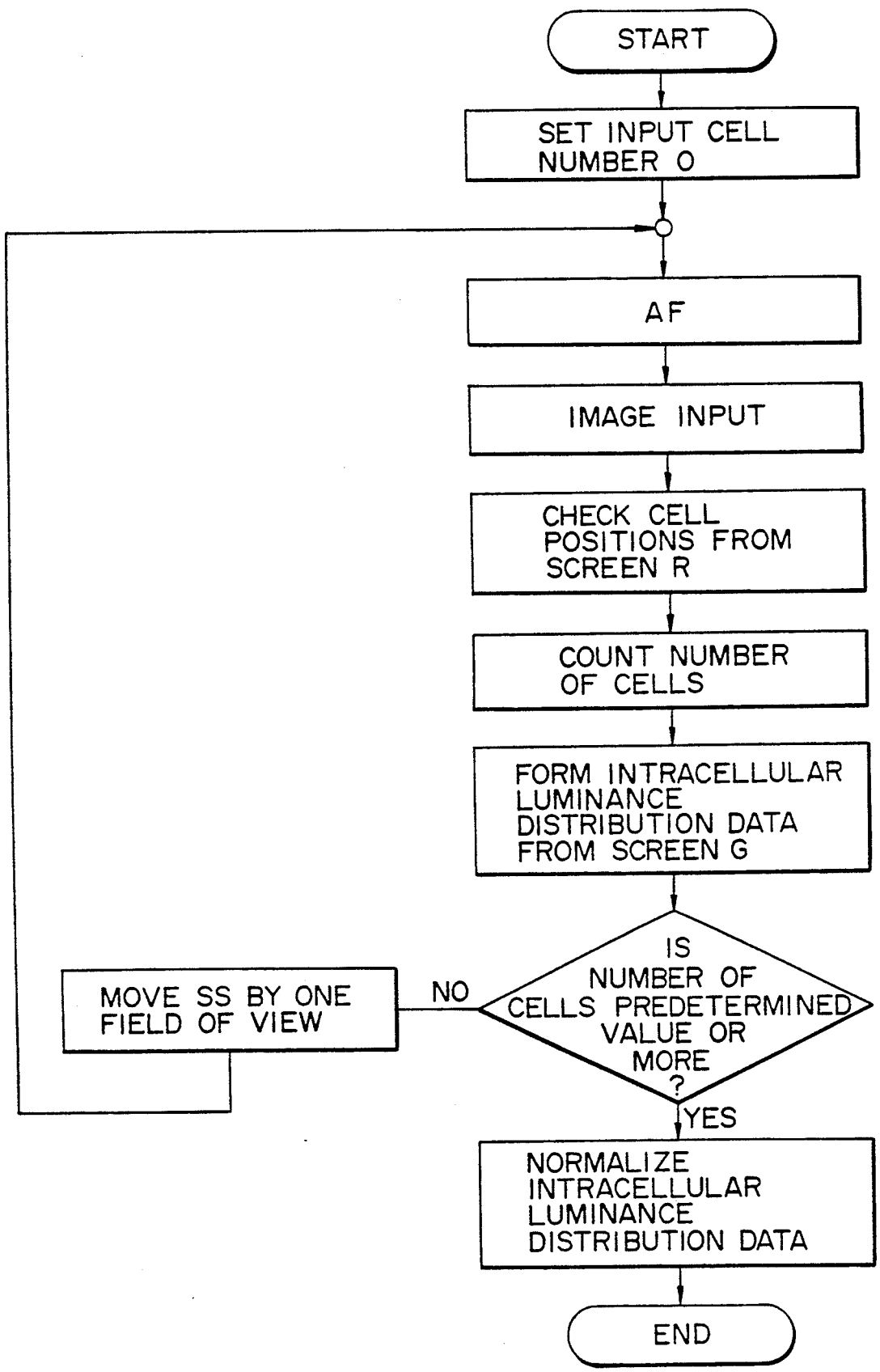
FIG. 3 is a flow chart for obtaining intracellular luminance distribution data.
Figure 4:
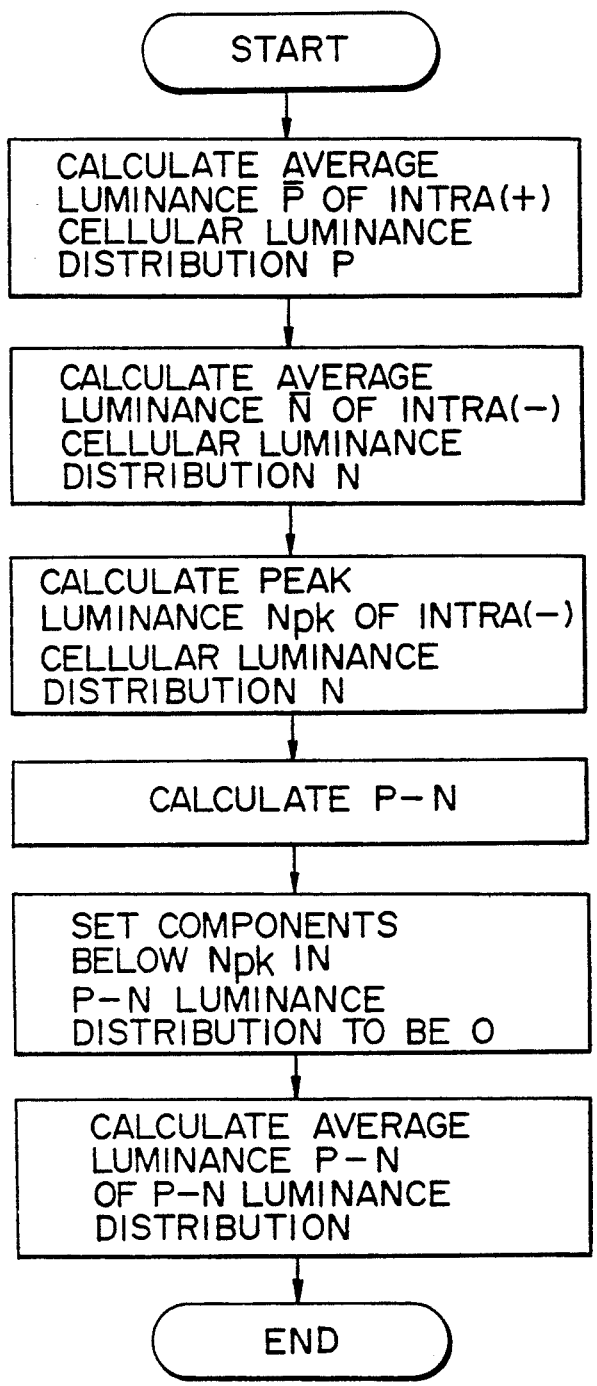
FIG. 4 is a flow chart for forming evaluation data.
Figure 7A:
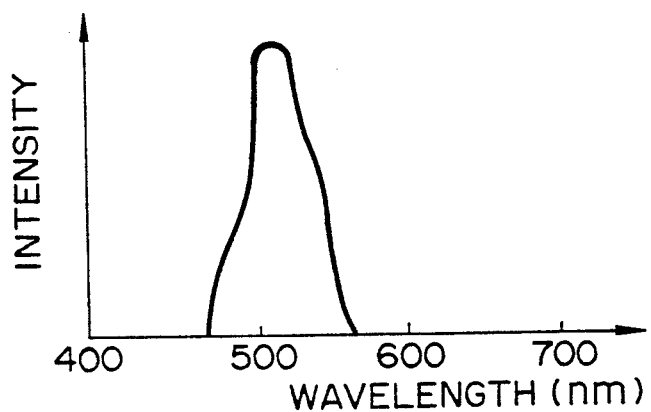
FIGS. 7A and 7B are graphs showing fluorescent wavelength characteristics of dyes a and b, respectively.
Figure 7B:
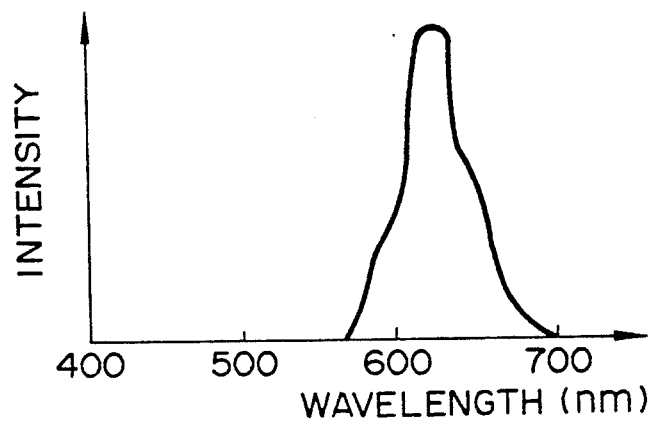

FIG. 3 shows an operation from formation of reference data up to virus infection determination. In this embodiment, cells as samples are dyed by an indirect fluorescent antibody method using a dye a having a fluorescent wavelength distribution shown in FIG. 7A and dyed using a dye b having a fluorescent wavelength distribution as shown in FIG. 7B. That is, the dyes a and b are recognized as green and red components, respectively, by the color TV camera 14.

The cells subjected to multiple dyeing using the dyes a and b are arranged in portions A, B, C, and D of the preparation. That is, (+)cells and (−)cells subjected to the multiple dyeing using a reference serum (a serum of a virus-infected body which is infected with a virus) and (+)cells and (−)cells subjected to the multiple dyeing using a serum of an object to be examined are arranged in the portions A and B and the portions C and D, respectively.

First, reference data is formed from the (+)cells (A) and the (−)cells (B) of the virus-infected body.

That is, the host computer 19 supplies a command to the autoloader 12 to load a preparation, which is set on the autoloader 12, on the SS 11. Subsequently, the SS 11 moves the portion A of the preparation, where the (+)cells of the virus-infected body are arranged, into the field of view of the microscope 13 in accordance with a command from the host computer 17. A red component of a sample image observed upon this manipulation and fetched in the frame memory 15 via the color TV camera 14 having the spectral sensitivity characteristics shown in FIG. 6 is obtained by the dye b. This sample image is a fluorescent image in which all cells emit light, as shown in FIG. 17B. A green component is obtained by the dye a. This sample image is a fluorescent image in which some cells emit light, as shown in FIG. 17A.

Subsequently, intracellular luminance distribution data is fetched from the image data of the sample A stored in the frame memory 15. This intracellular luminance distribution data fetch is performed on the basis of the flow chart shown in FIG. 3. That is, when the portion A of the preparation is moved into the field of view of the microscope 13, the microscope 13 is focused on the sample A, and the SS 11 is moved to store the image data of the portion A into the frame memory 15. The image data of the sample A stored in the memory 15 is transferred to the image processing unit 18 to recognize a cell in accordance with the red component of the image data. A luminance distribution (in units of pixels) of green components inside and outside the recognized cell is calculated and normalized (in units of %; therefore, entirely 100%). This luminance distribution will be called an intracellular luminance distribution hereinafter. In this manner, intracellular luminance distribution data of the portion A is obtained. The above operation is repeatedly performed while the SS 11 is moved in units of view fields until the number of cells in the portion A reaches a predetermined value. When the cell number reaches the predetermined value, the intracellular luminance distribution data is normalized.

Subsequently, the sample B of the virus-infected body is moved into the field of view of the microscope 13 to obtain intracellular luminance distribution data of the sample B.

When the intracellular luminance distribution data of the sample A as the (+)cells of the virus-infected body and the sample B a the (−)cells of the sample B are obtained as described above, a reference data calculation is executed. This reference data calculation is executed on the basis of the flow chart shown in FIG. 4.

Figure 8A:
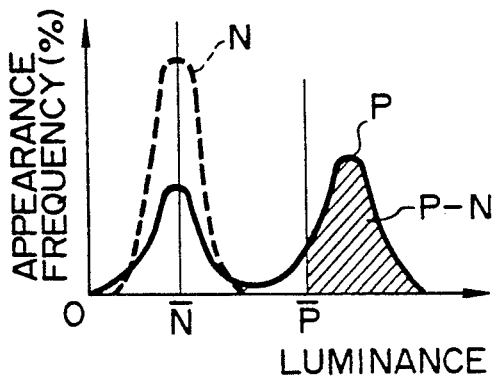
FIGS. 8A, 8B, 9A, 9B, 10A and 10B are graphs for explaining the presence/absence of infections on the basis of luminance distributions.
Figure 8B:
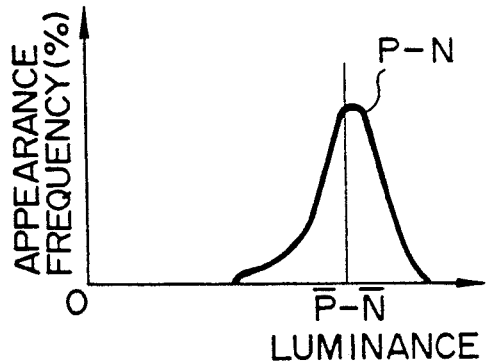

(P-N) is obtained such that the (−)cell luminance distribution N is subtracted from the (+)cell luminance distribution P, and components having levels corresponding to an N peak luminance Npk (about maximum appearance frequency) are further subtracted from the resultant difference. The (P-N) value corresponds to a hatched portion in each of FIGS. 8A to 10B, i.e., a value obtained by exracting only light-emitting portions. FIGS. 8A and 8B show luminance distributions obtained when the object to be examined is infected with a virus, FIGS. 9A and 9B show luminance distributions obtained when the object to be examined is not infected with a virus, and FIGS. 10A and 10B show luminance distributions obtained when a nonspecific reaction is caused.

As shown in FIGS. 8A and 8B, the luminance distributions obtained when the object to be examined is infected with a virus exhibit that a reacted portion emits strong light and has two peaks since only the (+)cells are subjected to an antigen-antibody reaction. Therefore, the (−)cell luminance distribution is concentrated in a low-luminance region.

Figure 9A:
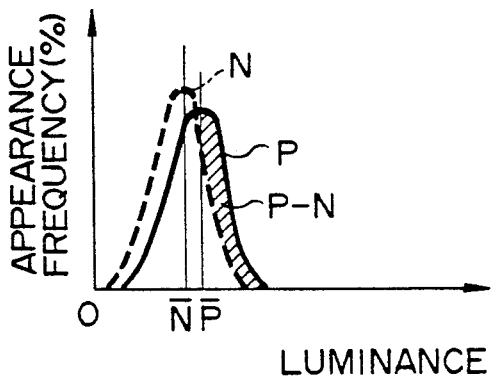
Figure 9B:
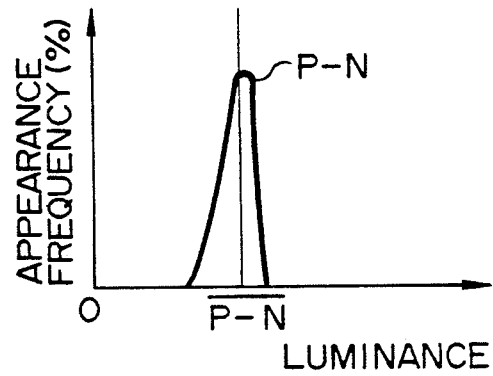

As shown in FIGS. 9A and 9B, the luminance distributions obtained when the object to be examined is not infected with a virus exhibit that (+)cell and (−)cell distributions are plotted in the low-luminance regions since neither (+)cells nor (−)cells are subjected to an antigen-antibody reaction.

Figure 10A:
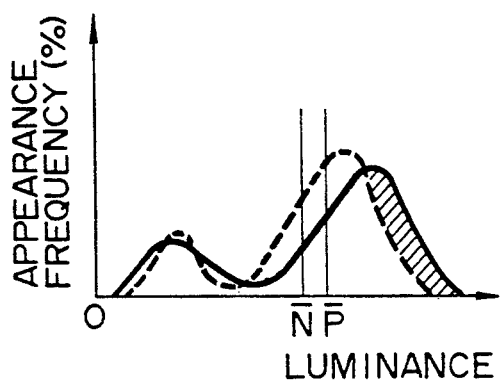
Figure 10B:
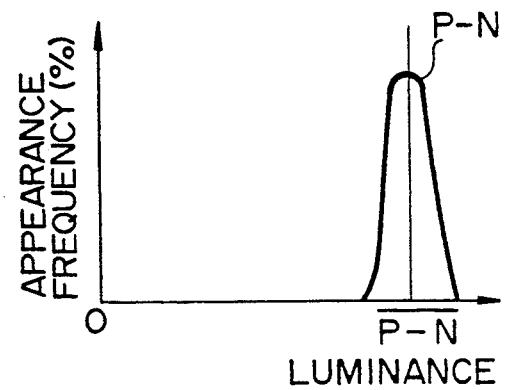

As shown in FIGS. 10A and 10B, the luminance distributions obtained when a nonspecific reaction is caused exhibit that luminances are also distributed in a high-luminance region since the antibodies of the (+)cells and (−)cells are bonded to each other.

In this embodiment, an average luminance P of the intracellular luminance distribution Pc of the sample A, an average luminance N of the intracellular luminance distribution Nc of the sample B, and the intra(−)cellular luminance distribution N peak luminance of the sample B are calculated. A difference (Pc-Nc) is then calculated, and data having luminance values of the peak luminance Npk or less are defined as "0" data. An average luminance of the luminance distribution (P-N) from which the data having luminance values of the peak luminance Npk or less are eliminated is obtained. The resultant average luminance N of the intra(−)cellular luminance distribution $\overline{N}$ and the resultant average luminance distribution $(\overline{P-N})$ are stored as reference data.

Evaluation data is calculated from the intracellular luminance distribution data of the samples C and D of the object.

The sample C of the preparation is moved to the field of view of the microscope 13, and intracellular luminance distribution data of the sample C is obtained on the basis of the flow chart in FIG. 3. An average luminance distribution $\overline{Pd}$ of the sample C, an average luminance distribution $\overline{Nd}$ of the sample D, and an average $(\overline{Pd-Nd})$ of differences (Pd-Nd) between the average luminance distributions Pd and Nd are calculated on the basis of the flow chart in FIG. 4.

Figure 11A:
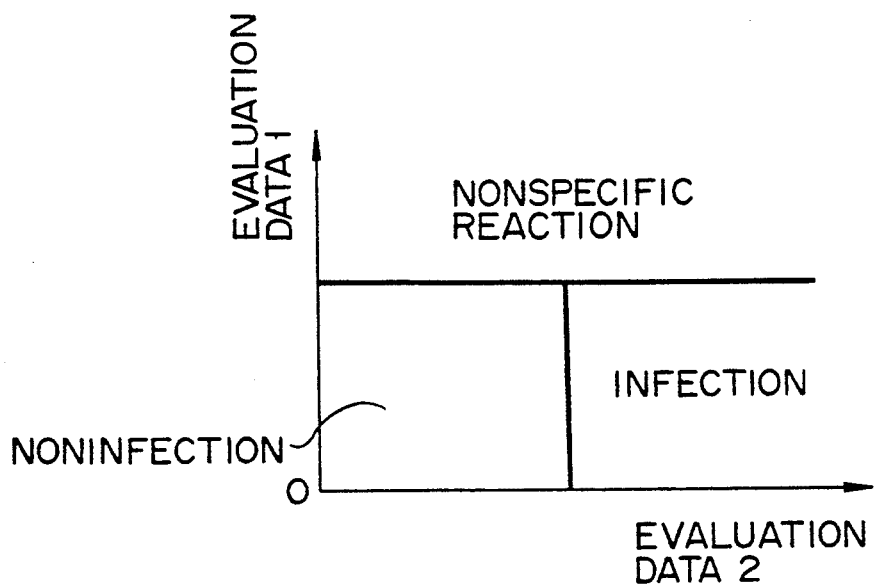
FIG. 11A is a view showing noninfection, infection, and nonspecific areas according to evaluation data 1 and 2.

A quotient $(\overline{Nd}/\overline{Nc})$ of the intra(−)cellular luminance distribution data $\overline{Nc}$ of the reference sample (B) of and the intra(−)cellular luminance distribution data $\overline{Nd}$ of the sample D of the object is defined as evaluation data 1, and a ratio $(\overline{Pd-Nd})/(\overline{Pc-Nc})$ is defined as evaluation data 2. Threshold values are determined for these evaluation data to perform determination, as shown in FIG. 11A.

The threshold values are determined as follows.

The apparatus is actually operated to output data prior to determination. The samples are observed and ranked by the examiner.

The data are ranked into five levels such as ① noninfection, ② undeterminable level, ③ infection (weak), ④ infection (medium), and ⑤ infection (strong).

A variance $\sigma_i^2$ of data within each rank or level is obtained to provide a variation width of $\pm n\sigma$ (n=appropriately 2 to 3) with respect to the center of the range.

At this time, area overlapping portions R1 and R2 such as hatched areas in FIG. 12A are defined as undeterminable areas. FIG. 12A shows threshold values set when evaluation data 1 is used, and FIG. 12B shows threshold values set when evaluation data 2 is used. By providing the undeterminable areas, a probability of an undeterminable state is increased, but a probability of determination errors can be largely reduced.

Figure 11B:
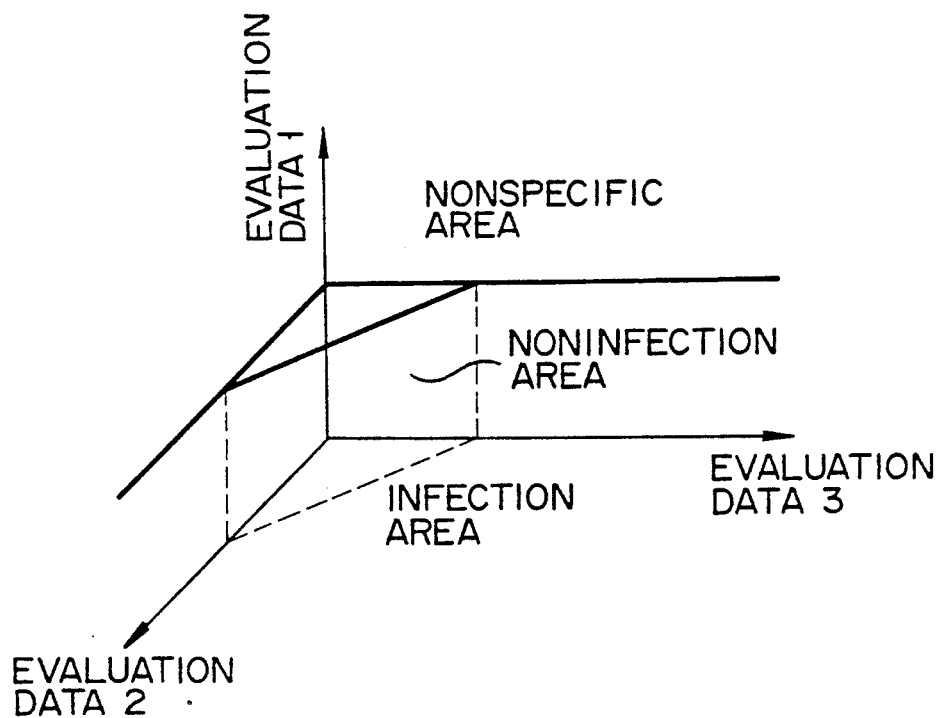
FIG. 11B is a view showing noninfection, infection and nonspecific areas according to evaluation data 1, 2, and 3.

Determination may be performed in consideration of the presence of, e.g., dust in a cell. A value obtained by dividing the area of (Pd-Nd) by the area of (Pc-Nc) may be defined as evaluation data 3 in FIG. 11B in consideration of the area of the dust or the like, and threshold values may be set, as shown in FIG. 11B. Evaluation data and threshold values used in the determination operations are determined in accordance with cell samples, types of dyes, and methods of forming samples.

Correspondences between objects and areas are determined in accordance with the evaluation reference including the above evaluation data and threshold values. When a given object belongs to an undeterminable area, a color image of cell groups of the samples A, B, C, and D is stored in the external memory unit 17. When a determination result represents that an object belongs to any one of the areas except for the undeterminable area, the area including the object is output to the external output unit 21.

In this embodiment, when a preparation is set, virus infections can be automatically determined without touching the objects, and loads on examiners can be largely reduced, and a large number of samples can be determined. At the same time, since the examiner need not touch the objects during examinations, secondary infection can be perfectly prevented.

A cell is dyed with a red dye to check it and is dyed with a blue dye to determine the presence/absence of infection, and the color TV camera 14 having spectral sensitivity characteristics matching to the fluorescent wavelength distributions of the two dyes is used. The fluorescent images are not adversely affected from each other and can be easily recognized. In addition, an intraference filter need not be arranged in the color TV camera, and the apparatus can be simplified as a whole. Green which is most stimulus to a human eye from three primaries is selected as a dye for determining the presence/absence of inflection, and red which is a largest contrast difference from green is selected as a dye for checking the cell position. Therefore, the fluorescent images can be easily judged.

Since reference samples are formed on a preparation of samples of objects to be examined, the same dyeing conditions are established, and more accurate determination can be performed.

Since image data of objects determined to belong to the undeterminable areas are stored in the external memory unit 17, the examiner can carefully examine these image data in the subsequent analysis and can make a final judgement.

Figure 13:
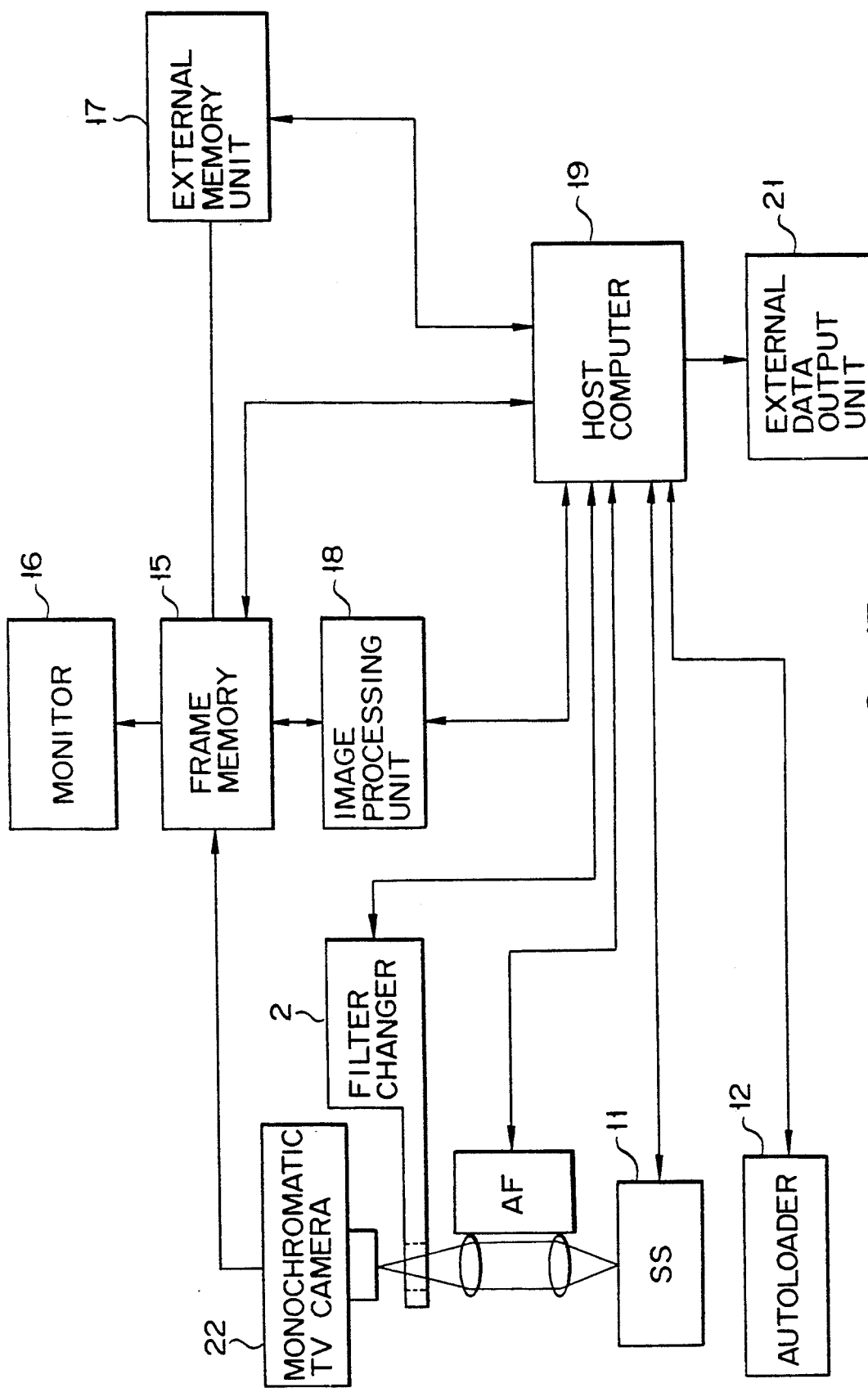
FIG. 13 is a block diagram showing an arrangement of a modification of the first embodiment.

In the above embodiment, the fluorescent wavelengths of the dyes are selected to correspond to spectral sensitivities of green and red of the color TV camera 13. If such selection is impossible, an intraference filter is arranged in a light-receiving portion of a monochromatic TV camera 22, as shown in FIG. 13. In this case, the intraference filter is automatically switched by a filter changer 23 to obtain the same function and effect as in this embodiment.

Even if fluorescent wavelength distributions of the dyes a and b overlap to a non-negligible degree, if all cells are uniformly dyed with the dye b, measured values may be regarded as values with simple offset values. Therefore, cells can be recognized and determined even from images falling within one wavelength range.

The second embodiment of the present invention will be described with reference to FIG. 14.

This embodiment exemplifies an operation for causing separate TV cameras to pickup (+)cell luminance data and (−)cell luminance data independently of each other. Cell samples are dyed with the same dyes a and b as in the first embodiment and are free from sample contamination caused by dyeing errors.

A (+)cell image is picked up by a color TV camera 31 and is output as R, G, and B video signals in response to timing signals output from an external synchronizing circuit 32. The R-component video signal has a high luminance level in a cell portion, i.e., has a high voltage. The G-component video signal has a high luminance level at a portion to which an antibody is bonded. The R- and G-component video signals output from the color TV camera 31 are input to a comparator 34 and a delay circuit 35, respectively, through a switching circuit 33. When the R-component video signal has a voltage higher than a reference voltage, a comparator output is set at high level to turn on the switching circuit 36 and to supply a constant voltage to an integrator 37. When the switching circuit 36 is turned on, the G-component video signal input to the delay circuit 35 is supplied to an integrator 38 through the switching circuit 36. The delay circuit 35 delays the G-component video signal until the R-component video signal is compared by the comparator 34 and the switching circuit 36 is turned on.

A value represented by an output from the integrator 38 is a total sum of G luminances, and a value represented by an output from the integrator 37 represents a total area of the cells.

The values from the integrator 37 and 38 are input to a divider 39. The divider 39 divides the total sum of the G luminances by the total area of the cells and outputs a quotient. That is, the divider 39 outputs a G-component intracellular average luminance.

An arrangement from reception of a (−)cell image by a color TV camera 41 to the output of the G-component intra(−)cellular average luminance from the divider 49 is the same as the (+)cell detection system described above.

The intra(−)cellular average luminance of the G-component as an output from the divider 49 is input to a comparator 50 set with a reference value for determining whether a nonspecific reaction is caused. The output from the divider 49 is compared with the reference value by the comparator 50 to determine whether a nonspecific reaction is caused. A determination result from the comparator 50 is input to a decoder 51.

The intra(+)cellular average luminance output from the divider 39 and the intra(−)cellular average luminance output from the divider 49 are input to a divider 52. The divider 52 divides the intra(+)cellular average luminance value by the intra(−)cellular average luminance and outputs a quotient to comparators 53 and 54. Reference values are set in the comparators 53 and 54 and are compared with the output from the divider 52, thereby determining infection, noninfection, or an undeterminable state. Outputs from the comparators 53 and 54 are output to the decoder 51. Note that the reference voltages of the comparators 50, 53, and 54 are determined by the same method as in the first embodiment.

The decoder 51 outputs a determination result on the basis of the outputs from the comparators 50, 53, and 54 by a trigger pulse output from a decode trigger generator 55 synchronized with a timing signal output from the external synchronizing circuit 32 at the end of measurement.

Upon completion of the measurement, a clear trigger generator 56 generates a trigger pulse to clear the integrator 37, 38, 47, and 48. A switch driver 57 serves as a circuit for turning on/off the switching circuits 33 and 43 to prevent data from being supplied to the integrator in a non-measurement state.

According to the second embodiment, since a data processing system is constituted by an analog circuit and no digital processing is performed, the overall circuit can be arranged without using relatively expensive A/D converters and a relatively expensive digital computer, resulting in low cost.

Sample images of the (—)cells and (+)cells are simultaneously received by the two TV cameras 31 and 41, and the examination results can be output in real time by sequential analog processing. Therefore, the examination speed can be increased, and the examination time can be largely shortened.

As has been described above, according to the present invention, there is provided a virus infection examination apparatus wherein a large number of samples can be automatically processed, the loads on examiners can be largely reduced, and a highly reliable determination result can be obtained.

The cell position is checked by the fluorescent image obtained by dyeing cells in the second dyeing process, and virus infections of objects can be examined by the fluorescent images obtained by dyeing the cells in the first dyeing process. The fluorescent images can be easily determined, and the cell positions can be easily checked. Accurate determination can be performed, loads on examiners can be largely reduced, and the fluorescent wavelength distributions of the dyes are matched with the spectral characteristics of the image pickup means. There is, therefore, provided a virus infection examination method capable of further reducing the size of an apparatus.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A virus infection examination apparatus comprising:
   a microscope for observing fluorescent images of antigen positive and negative cells dyed with a fluor by an indirect fluorescent antibody method using a serum of an object to be examined;
   image pickup means for converting the fluorescent images as observation images of said microscope into image data;
   detecting means for processing the image data obtained by said image pickup means and detecting fluorescent luminance distributions of the antigen positive and negative cells; and
   means for determining the presence/absence of a virus infection of the object on the basis of a difference between the fluorescent luminance distributions detected by said detecting means.

2. An apparatus according to claim 1, wherein said determining means comprises means for comparing a fluorescent luminance distribution difference between the antigen positive and negative cells of a virus-infected body with the fluorescent luminance distribution difference between the antigen positive and negative cells of the object, and for determining the presence/absence of the virus infection of the object 3. An apparatus according to claim 1, wherein said image pickup means comprises a color TV camera for recognizing respective dyes for dyeing the antigen positive and negative cells as primary color components.

4. An apparatus according to claim 1, wherein said image pickup means comprises a monochromatic TV camera, a plurality of intraference filters, and a filter changer for switching said plurality of intraference filters in correspondence with the respective dyes for dyeing the antigen positive and negative cells.

5. An apparatus according to claim 1, wherein said image pickup means includes first and second TV cameras for independently receiving luminance data of the antigen positive cell and luminance data of the antigen negative cell, and said detecting means includes an analog circuit for processing outputs from said first and second TV cameras in an analog manner.

* * * * *